US012806107B2

(12) United States Patent
Gloger

(10) Patent No.: US 12,806,107 B2
(45) Date of Patent: Nov. 24, 2026

(54) MEDIAL UNILATERAL EXOSKELETON

(71) Applicant: MEBSTER S.R.O., Prague (CZ)

(72) Inventor: Michal Gloger, Ostrava (CZ)

(73) Assignee: MEBSTER S.R.O., Prague (CZ)

(*) Notice: Subject to any disclaimer, the term of this patent is extended or adjusted under 35 U.S.C. 154(b) by 1352 days.

(21) Appl. No.: 17/633,436

(22) PCT Filed: May 29, 2020

(86) PCT No.: PCT/EP2020/065092
§ 371 (c)(1),
(2) Date: Feb. 7, 2022

(87) PCT Pub. No.: WO2020/240026
PCT Pub. Date: Dec. 3, 2020

(65) Prior Publication Data

US 2022/0287904 A1 Sep. 15, 2022

(51) Int. Cl.
*A61H 1/00* (2006.01)
*A61F 5/01* (2006.01)
(Continued)

(52) U.S. Cl.
CPC ......... *A61H 1/0262* (2013.01); *A61F 5/0102* (2013.01); *A61H 3/008* (2013.01);
(Continued)

(58) Field of Classification Search
CPC ... A61H 1/0262; A61H 1/0266; A61F 5/0102; A61F 5/0123; A61F 5/0125; A61F 5/0127; A61F 5/013
See application file for complete search history.

(56) References Cited

U.S. PATENT DOCUMENTS 10,080,697 B2 * 9/2018 Swift ..................... B25J 9/0006
10,213,356 B2 * 2/2019 Glaister .................. A61H 3/00
(Continued)

FOREIGN PATENT DOCUMENTS

JP 2003135542 A 5/2003
JP 2007020909 A 2/2007
(Continued)

OTHER PUBLICATIONS

International Search Report related to PCT/EP2020/065092; reported on Sep. 14, 2020.
(Continued)

*Primary Examiner* — LaToya M Louis

(57) ABSTRACT

A one-sided exoskeleton for placement in the center of a body of a person. The exoskeleton has a medial hip joint that includes hip plates and hip pulleys, a plurality of actuation cables, orthoses suitable for a right and a left lower limb of a person. Each of the orthoses comprising an ankle joint having a replaceable stirrup with a shoe or a shoe insert, a stirrup coupling, an ankle joint body and a guide pulley. Each of the hip pulleys is coupled to a respective ankle joint by at least one actuation cable of the plurality of actuation cables so that each actuation cable is on one end attached to one of the hip pulleys and on a second end attached to the stirrup coupling of the respective ankle joint. Each of the actuation cables is configured to convey a movement of the hip pulley to the respective ankle joint and cause a pivot of the respective replaceable stirrup in a first direction.

20 Claims, 11 Drawing Sheets

(51) Int. Cl.
*A61H 1/02* (2006.01)
*A61H 3/00* (2006.01)

(52) U.S. Cl.
CPC .................. *A61H 2003/007* (2013.01); *A61H 2201/0192* (2013.01); *A61H 2201/1215* (2013.01); *A61H 2201/165* (2013.01); *A61H 2201/1676* (2013.01); *A61H 2203/0406* (2013.01)

(56) References Cited

U.S. PATENT DOCUMENTS

| | | | | |
|---|---|---|---|---|
| 2015/0289997 | A1* | 10/2015 | Bosscher | B25J 9/0006 623/24 |
| 2016/0128890 | A1* | 5/2016 | LaChappelle | A61H 3/00 623/30 |
| 2017/0209330 | A1* | 7/2017 | Hughes | A61H 1/0266 |
| 2018/0055712 | A1* | 3/2018 | Gayral | A61H 1/0266 |
| 2022/0110814 | A1* | 4/2022 | Mooney | A61B 5/0022 |
| 2022/0192846 | A1* | 6/2022 | Mooney | A61H 3/00 |
| 2022/0241131 | A1* | 8/2022 | Papania-Davis | F16H 19/0645 |
| 2022/0273515 | A1* | 9/2022 | Tucker | A61H 3/008 |
| 2022/0347040 | A1* | 11/2022 | Mooney | A61H 1/0266 |
| 2022/0401285 | A1* | 12/2022 | Murphy | A61F 5/0111 |
| 2023/0381049 | A1* | 11/2023 | Lai | A61H 1/0266 |

FOREIGN PATENT DOCUMENTS

| | | | |
|---|---|---|---|
| JP | 2010063632 | A | 3/2010 |
| JP | 2018187083 | A | 11/2018 |
| WO | 2012125765 | A2 | 9/2012 |

OTHER PUBLICATIONS

Priority Application Search Report related to Application No. PV 2019-334; reported on Sep. 4, 2019.

* cited by examiner

MEDIAL UNILATERAL EXOSKELETON

CROSS-REFERENCE TO RELATED APPLICATION

This Application is a 35 USC § 371 US National Stage filing of International Application No. PCT/EP2020/065092 filed on May 29, 2020 and claims priority under the Paris Convention to Czech Patent Application No. PV 2019-334 filed on May 30, 2019.

FIELD OF THE DISCLOSURE

The present disclosure generally relates to the field of devices and rehabilitation assistive technologies for persons with severe lower limb immobility, such as paraplegics. The present disclosure is particularly useful for a rehabilitation and a walk enablement of persons with spinal cord injuries.

BACKGROUND OF THE DISCLOSURE

This section provides background information related to the present disclosure which is not necessarily prior art.

Persons with spinal cord injuries who had a severe or a partial paralysis of the lower limbs need to start with exercise of the paralyzed body segments as soon as possible and verticalize themselves to prevent further health complications due to prolonged sitting such as for instance osteoporosis of the lower limbs, muscle atrophy or bedsores. Such additional health complication causes further discomfort and make the overall treatment very expensive and time consuming.

Passive movement of the lower limbs during rehabilitation can be performed either with an assistance of another person or by a dedicated device. With approximately five hundred thousand spinal cord injuries worldwide each year, resulting in paraplegia in approximately 40% of the injuries, there is a significant need for a universal, inexpensive, easy-to-maintain, and easy-to-use device to allow verticalization of the injured person and his or her gait training with only a limited assistance or even without assistance from third person such as a healthcare professionals.

Currently available rehabilitation assistive technologies include parapodia and conventional lateral exoskeletons consisting of two orthoses, connecting the hips and ankles joints. Typical disadvantages of these assistive technologies are high weight, size and an amount of time it takes don and doff an assistive technology which in most cases requires a need for a third-party assistance. Further drawbacks of the current assistive technologies are time required to adjust an assistive technology to a specific person and importantly an affordability of an assistive technology as in many countries such assistive technologies are not covered by a health insurance and the current assistive technologies are price prohibitive.

Therefore, it would be advantageous to have an assistive technology that takes into account at least some of the issues discussed above as well as possibly other issues.

SUMMARY OF THE DISCLOSURE

One objective of the present disclosure is to remedy at least part of the above identified drawbacks. An aspect of the present disclosure is directed to a medial unilateral exoskeleton having a medial hip joint. The medial hip joint comprising hip plates and hip pulleys, a plurality of actuation cables, orthoses suitable for a right and a left lower limb of a person, the orthoses being coupled to the hip joint and each of the orthoses comprising an ankle joint having a replaceable stirrup with a shoe or a shoe insert, an stirrup coupling, an ankle joint body and a guide pulley. Each of the hip pulleys is coupled to a respective ankle joint by at least one actuation cable of the plurality of actuation cables so that each actuation cable is on one end attached to one of the hip pulleys and on a second end attached to the stirrup coupling of the respective ankle joint, wherein the replaceable stirrup is pivotably connected to the ankle joint body via the stirrup coupling, wherein the guide pulley is coupled to the ankle joint body and configured to support and direct a respective actuation cable of the plurality of actuation cables to the stirrup coupling, wherein each of the actuation cables is configured to convey a movement of the hip pulley to the respective ankle joint and cause a pivot of the respective replaceable stirrup in a first direction.

In another aspect, each of the orthoses further comprises at least one elastic member having a one end coupled to the ankle joint body and a second end coupled to the stirrup coupling, wherein the at least one elastic member is adapted to act in a second direction opposite to the first direction caused by the movement conveyed by the respective actuation cable.

In another aspect, each of the actuation cable is either a pull cable or a push-pull cable and each of the actuation cable has a solid or wire rope core.

In another aspect, each of the plurality of actuation cables or at least one actuation cable of the plurality of actuation cables is a Bowden cable.

In another aspect, each of the orthoses further comprises a biasing cable and a moveable member. The one end of the elastic member is coupled to the ankle joint body via the moveable member. A one end of the biasing cable is coupled to the moveable member and a second end of the biasing cable is coupled to the hip pulley and the biasing cable is adapted to position the moveable member so that the distance between both ends of the elastic member remains constant.

In another aspect, wherein each of the orthoses further comprises a linear guide coupled with the moveable member.

In another aspect, the linear guide comprises at least one of a rail linear guide, a linear bearing slide, a ball bearing slide, a rack slide, a dovetail slide or a roller slide.

In another aspect, each of the orthoses further comprises a hollow first part having a slot and a second part. The hollow first part is coupled to the ankle joint body and a portion of the second part is inserted within the first part. A portion of the moveable member is guided within the slot and engages the portion of the second part within the hollow first part.

In another aspect, the first part is a first hollow profile extending in a longitudinal direction, the second part is a second hollow profile extending in the longitudinal direction and is slidably engaged into the first hollow profile, the slot extends in the longitudinal direction.

In another aspect, the moveable member comprises a roller configured to roll on a guiding profile formed in the portion of the second part within the first hollow part, the guiding profile extending along the longitudinal direction.

In another aspect, the elastic member is formed by one or more elastic elements shaped as a belt, a band, a string, a rope or a spring or a combination thereof.

In another aspect, the movable member extends between two ends perpendicular to the longitudinal direction, and the medial unilateral exoskeleton includes two elastic members which are attached to the ends of the moveable member.

In another aspect, each of the hip pulleys is coupled to a respective ankle joint by means of one actuation cable of the plurality of actuation cables.

In another aspect, each of the orthoses further comprises a unilateral medial thigh upright, a thigh cuff comprising one or more thigh bands, a knee joint, an unilateral medial lower leg upright and at least one lower leg cuff.

In another aspect, the knee joint is a self-locking joint. The self-locking knee joint may be configured to automatically lock when the exoskeleton is attached to a standing person or when the person stands up from a seating position. The self-locking knee join may be adapted to lock the medial thigh upright and the lower leg upright rigidly together.

In another aspect, each of the actuation cables is at least partially embedded within the medial lower leg upright and/or the medial thigh upright. The medial lower leg upright and the medial thigh upright are configured to enable an attachment of the exoskeleton to a person.

In another aspect, the medial thigh upright and/or the medial lower leg upright have an adjustable length.

In another aspect, the ankle joint is provided with at least one adjustable element formed by an ankle adjusting screw adapted to provide a tension to the actuation cable coupled to the ankle joint and impact the angle in the ankle joint.

In another aspect, the medial hip joint is provided with at least one adjustable element formed by a hip adjusting screw. The at least one adjustable element is adapted to secure a tension of the actuation cable and impact angle of the ankle joint.

In another aspect, the medial unilateral exoskeleton further comprising a lumbar orthosis coupled to the medial hip joint or a lateral hip joint.

A further aspect is directed to a use of the medial unilateral exoskeleton apparatus as defined above, where the orthoses are connected respectively to a right and a left lower limb of a person and the shoe or shoe insert is connected to a foot of the person.

Further areas of applicability will become apparent from the description herein. The description and specific examples in the summary are intended for purposes of illustration only and are not intended to limit the scope of the present disclosure.

BRIEF DESCRIPTION OF THE DRAWINGS

Other features and advantages of the invention appear from the following detailed description of some of its embodiments, given by way of non-limiting example, and with reference to the accompanying drawings, in which.

DETAILED DESCRIPTION

Figure 1A:
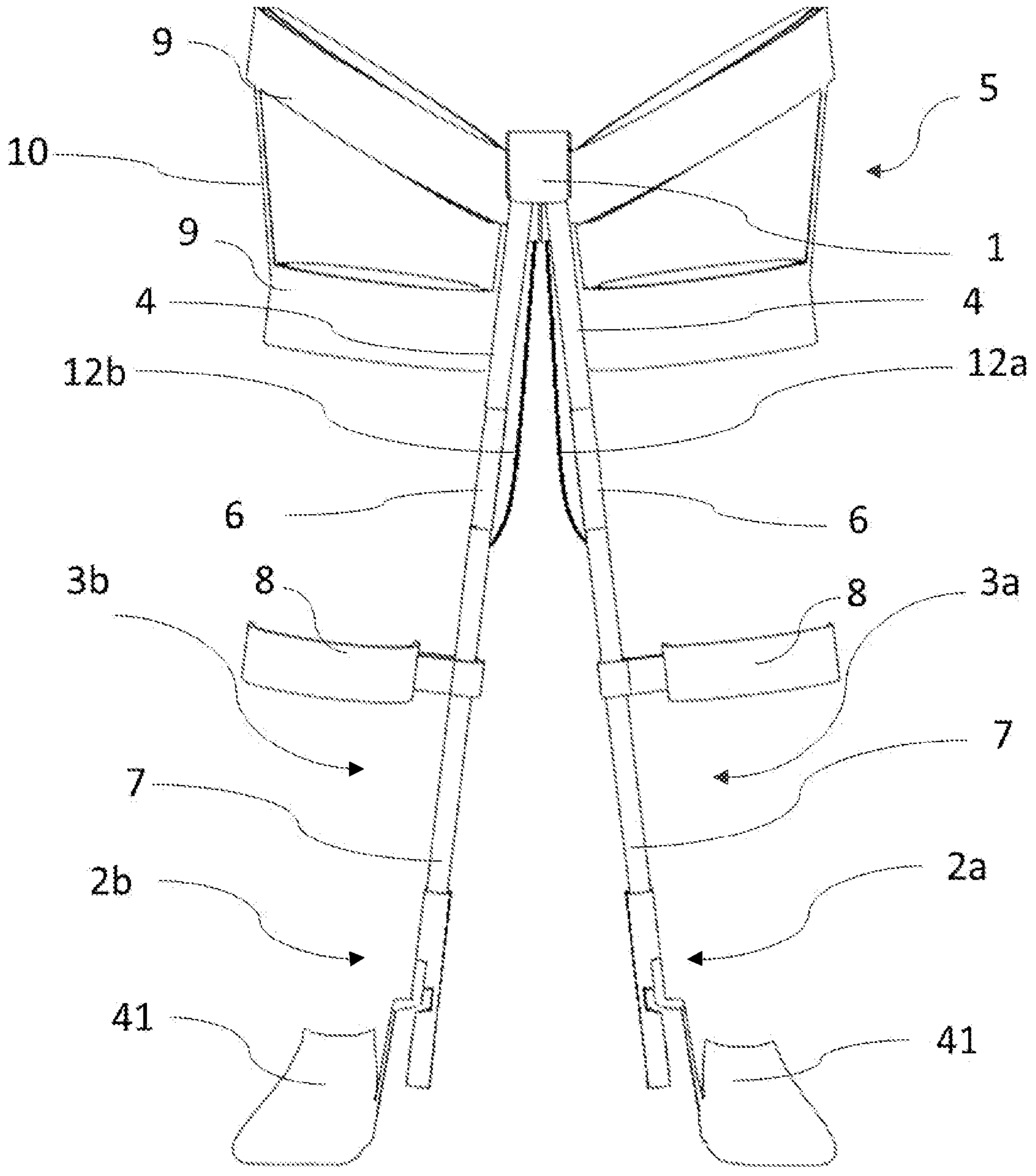
FIG. 1*a* is a front view depicting an embodiment of a medial unilateral exoskeleton.

The foregoing summary, as well as the following detailed description of certain examples will be better understood when read in conjunction with the appended drawings. As used herein, an element or step recited in the singular and proceeded with the word "a" or "an" should be understood as not excluding plural of the elements or steps, unless such exclusion is explicitly stated. Further, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional elements not having that property.

In the figures, the same references denote identical or similar elements, unless stated otherwise. In the drawings, the size of each element or a specific portion constituting the element is exaggerated, omitted, or schematically shown for convenience and clarity of description. Thus, the size of each component may not entirely reflect the actual size. In the case where it is judged that the detailed description of the related known functions or constructions may unnecessarily obscure the gist of the present disclosure, such explanation will be omitted.

The term medial unilateral exoskeleton relates to a one-sided exoskeleton for placement in the center of a body of a person. Such exoskeleton abuts the lower limbs only from the medial, i.e. the inner side of the limb. That way the medial unilateral exoskeleton ensures a more comfortable use of the exoskeleton for persons that suffer from swelling and/or skin problems where the use of bilateral orthoses that surround the limbs would be more complicated or even excluded.

Figure 2A:
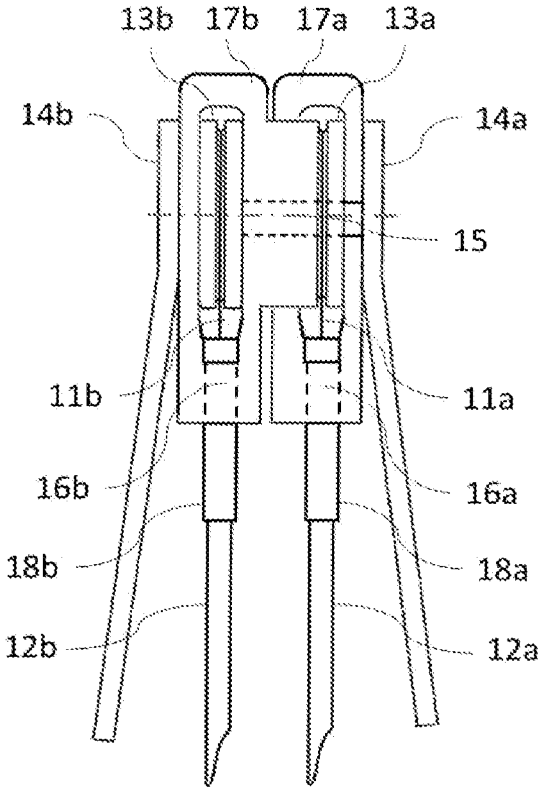
FIG. 2*a* is a front detail view depicting a detail of an embodiment of the medial hip joint of FIGS. 1*a* and 1*b*.
Figure 2B:
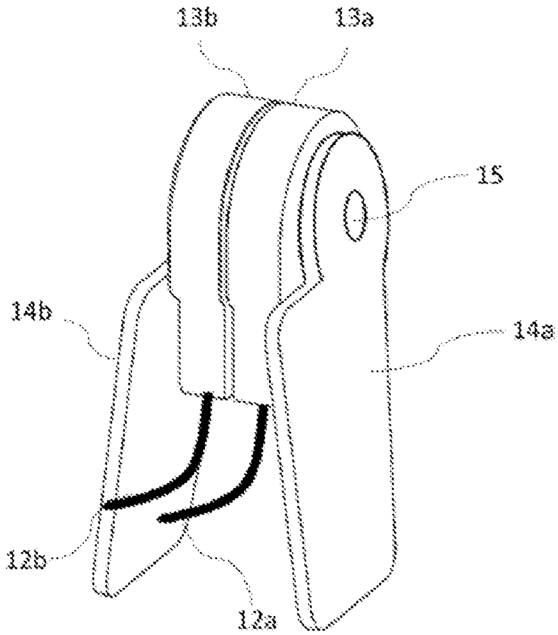
FIG. 2*b* is a perspective view of the detail of FIG. 2*a*.

FIG. 1*a* is a front view depicting an embodiment of a medial unilateral exoskeleton. The embodiment of the medial unilateral exoskeleton comprises a medial hip joint 1 comprising the hip plates 14*a*, 14*b* and hip pulleys 13*a*, 13*b* as shown in FIGS. 2*a* and 2*b*. The embodiment further comprises plurality of actuation cables 12*a*, 12*b* and orthoses 3*a*, 3*b*. Each actuation cable of the plurality of actuation cables 12*a*, 12*b* may be either a pull cable or a push-pull cable and each actuation cable of the plurality of actuation cables 12*a*, 12*b* may have a solid or wire rope core. Optionally the actuation cable may be only a wire rope. The solid or wire rope core of the actuation cable may be made from a steel, a stainless steel, a Kevlar, a carbon composite, aramid or any other suitable material. The core may be coated for instance by a PTFE material such as Teflon or the core may be a self-lubricated core to lower friction of the core when please within the cable. Each actuation cable of the plurality of actuation cables 12*a*, 12*b* or at least one cable of the plurality of actuation cables may be a Bowden cable. The actuation cables 12*a*, 12*b* may be at least partially embedded within the orthoses 3*a*, 3*b*.

Figure 1B:
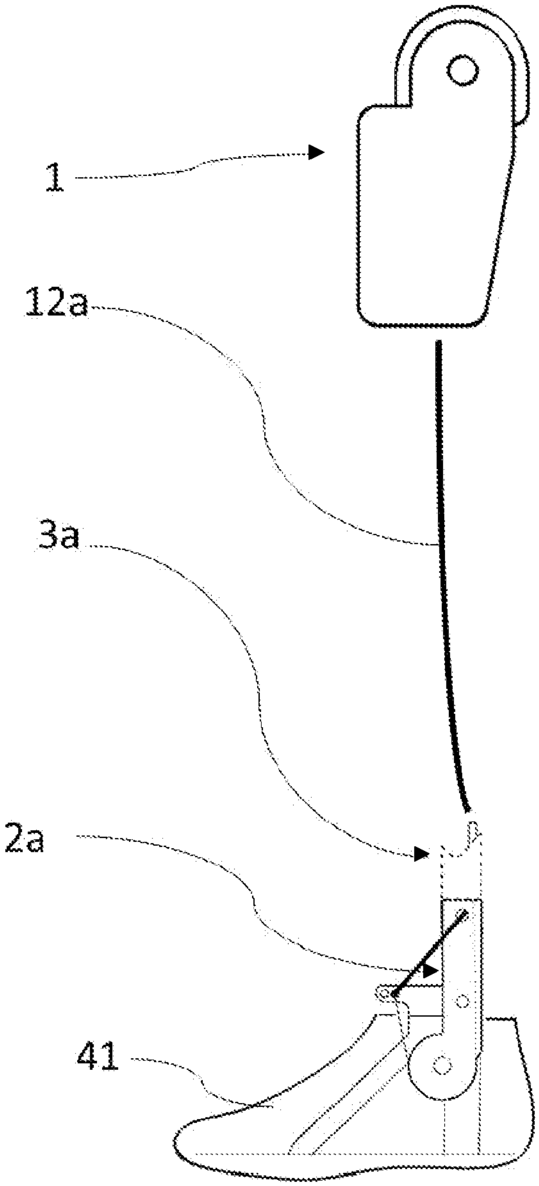
FIG. 1B is a simplified side view depicting the embodiment of the medial unilateral exoskeleton of FIG. 1*a*.
Figure 3:
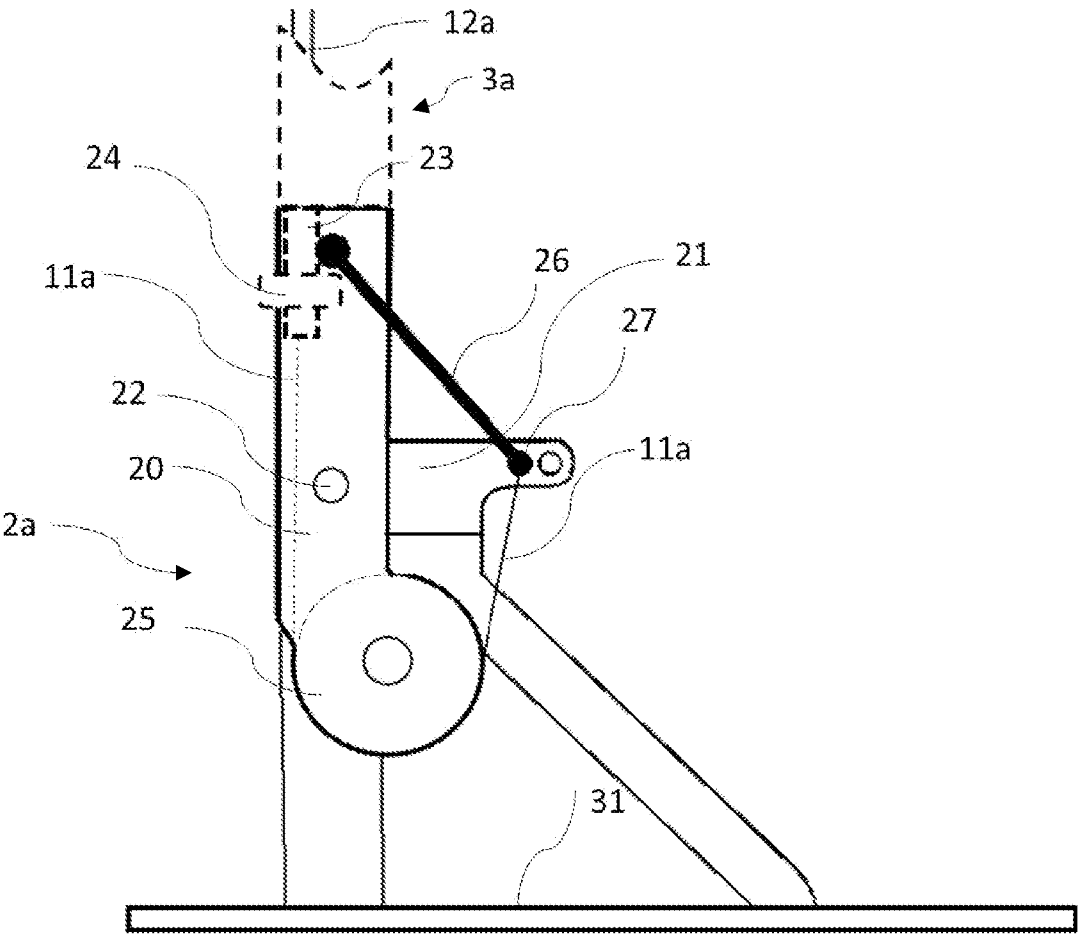
FIG. 3 is a side view depicting the arrangement of the ankle joint in the embodiment of FIG. 1*a*.
Figure 10:
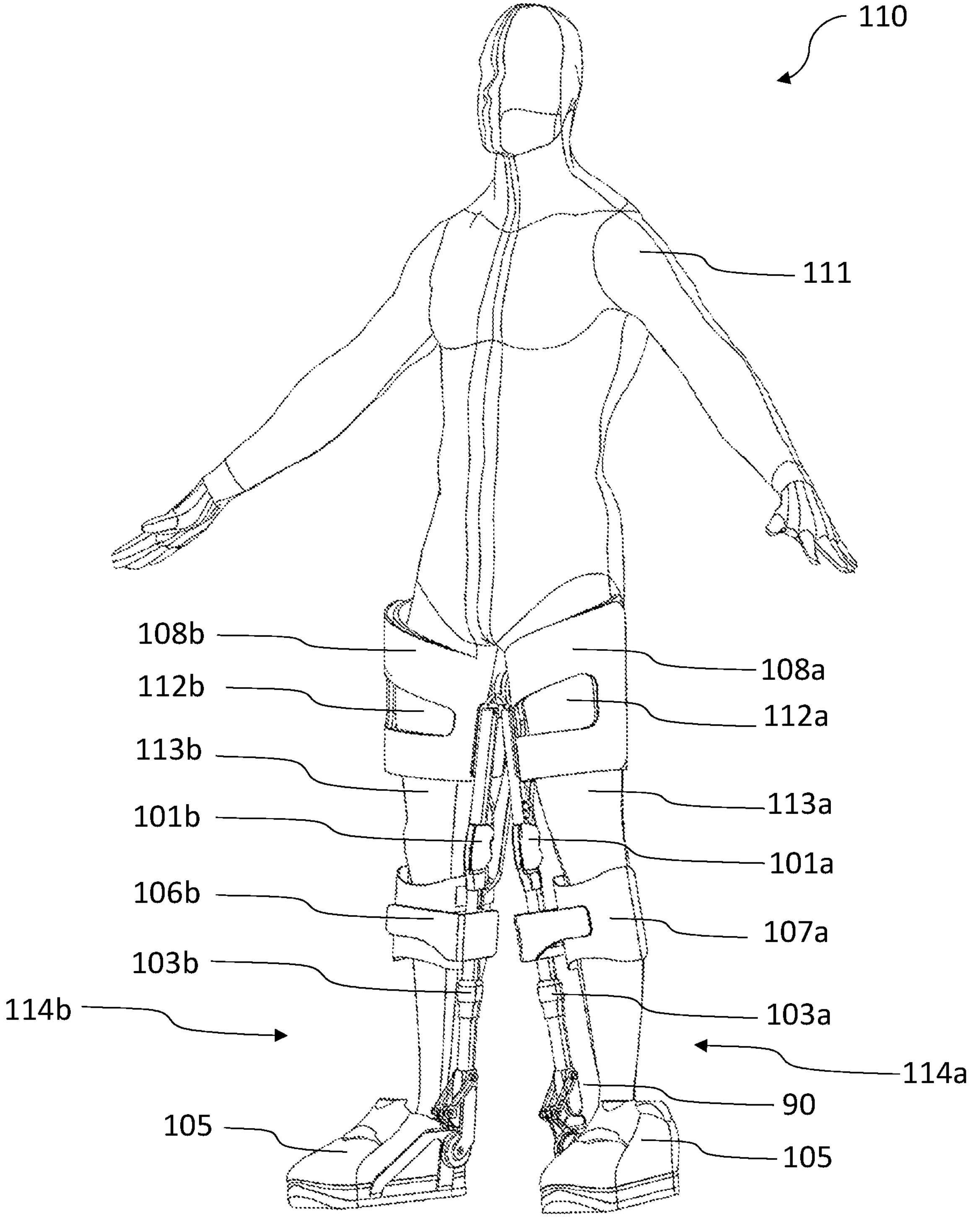
FIG. 10 is a perspective view depicting the embodiment of the medial unilateral exoskeleton of FIG. 9, attached to a person.

The orthoses may include a right unilateral orthosis 3*b*, 114*b* and a left unilateral orthosis 3*b*, 114*a*. As shown in FIG. 10 the orthoses 114*b*, 114*a* are suitable for a right 113*b* and a left lower limb 113*a* of a person 111, the orthoses are coupled to the medial hip joint 1 and as depicted in FIG. 1*a* each of the orthoses 3*a*, 3*b* comprising an ankle joint 2*a*, 2*b*. Each ankle joint 2*a*, 2*b* as depicted in FIGS. 1*b* and 3*a* comprises a replaceable stirrup 31 with a shoe 41 or a shoe insert 31, a stirrup coupling 21, an ankle joint body 20 and a guide pulley 25, 68. Each of the ankle joints 2*a*, 2*b* as exemplary depicted in FIG. 3 may be connected to one of the orthoses 3*a*, 3*b*. The stirrup coupling 21 may be rotatably coupled to an ankle pin 22. The ankle pin may be adapted to enable the stirrup coupling to pivot about the axis of the ankle pin 22 in direction d. Such pivot translates into a pivotable movement of the replaceable stirrup 31 in relation to the ankle joint body 20. Each of the orthoses may further comprise at least one elastic member 26 having a one end coupled to the ankle joint body 20 and a second end coupled to the stirrup coupling 21. The at least one elastic member 26 may be adapted to act in a second direction opposite to the first direction caused by the movement conveyed by the respective actuation cable 12*a*, 12*b*. The elastic member may be formed by one or more elastic elements shaped as a belt, a band, a ring, a string, a rope or a spring or a combination thereof. One benefit of the elastic member is that it enables a more flexible and more natural movement when walking in the medial unilateral exoskeleton as muscles of the person walking in the exoskeleton are more naturally activated whilst the walk stability being maintained Another benefit of the elastic element is that it can be easily changed or replaced to fit the needs of a person.

Each of the unilateral orthoses may further comprises a unilateral medial thigh upright 4, a thigh cuff 5 comprising one or more thigh bands 9, a knee joint 6, an unilateral medial lower leg upright 7 and at least one lower leg cuff 8. The unilateral medial thigh upright 4 and unilateral medial lower leg upright 7 may be either solid or hollow and may have any suitable cross-section, with oval or round cross-sections being preferred, since they do not contain any potentially sharp edges. The unilateral medial thigh upright 4 and unilateral medial lower leg upright 7 may be made of any solid material.

For ease of maintenance and handling it advantageous when the material is as light as possible. Suitable materials may be light and/or solid metals or composite materials. The one or more thigh bands 9 and at least one lower leg cuff 8 may be made of any suitable material either that is either flexible or rigid. Suitable materials may be steel, Kevlar or a carbon composite. For fastening to the limb can be used e.g. Velcro or a buckle, or other means that allow tightening bands cuffs to the limb regardless of the size of the circumference of the limb. The one or more thigh cuffs 5 may be replaced by unlocking a locking pin, extending the one or more thigh cuffs and snapping in a different cuffs size. In the same way, the at least one lower leg cuff 8 may be replaced. The knee joint 6 may be a self-locking joint. Such self-locking joint may enable the medial unilateral exoskeleton handling as well as it simplifies the attachment of the exoskeleton to a seated person. The self-locking knee joint 6 may be adapted to lock the medial thigh upright 4 and the lower leg upright 7 rigidly together. One benefit of the self-locking knee joint is to automatically lock the joint whilst the exoskeleton is attached to a standing person.

Figure 4:
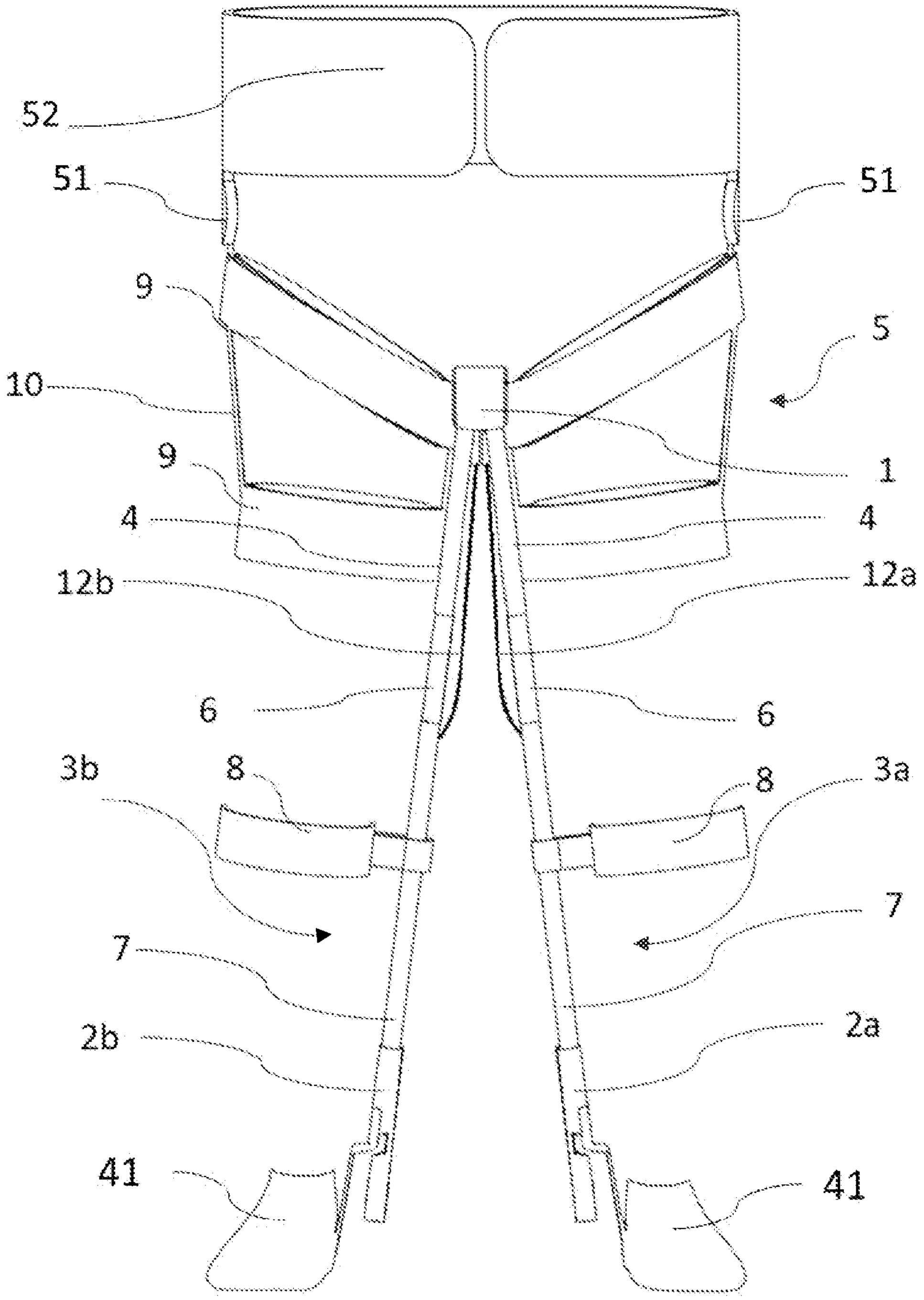
FIG. 4 is a front view depicting the embodiment of the medial unilateral exoskeleton of FIG. 1*a* further equipped with a lumbar orthosis.

At least one or each of the plurality of actuation cables may be at least partially embedded within the medial lower leg upright 7 and/or the medial thigh upright 4. At least one of the medial thigh upright 4 and/or the medial lower leg upright 7 may have an adjustable length. The adjustable length is controlled by a length adjusting member shown 103*a*, 103*b* shown in FIG. 9 or 10. Each orthosis may have one or more length adjusting members. As depicted in FIG. 4 in one embodiment the medial unilateral exoskeleton may further comprise a lumbar orthosis 52 coupled to the medial hip joint 51 or a lateral hip joint 51. One benefit of such arrangement is a stability improvement of a person having the exoskeleton attached. The lumbar brace connected to the lateral hip joint or medial hip joint may comprise a back support, a bandage and a Velcro fastening and may further include one or more shoulder straps for better spine stabilization.

As shown in FIGS. 2*a*, 2*b* and 3*a* each of the hip pulleys 13*a*, 13*b* may be coupled to a respective ankle joint 2*a*, 2*b* by at least one actuation cable 12*a*, 12*b* of the plurality of actuation cables so that each actuation cable is on one end attached to one of the hip pulleys 13*a*, 13*b* and on a second end attached to the stirrup coupling 21 of the respective ankle joint. Each of the hip pulleys may be coupled to a respective ankle joint by means of one actuation cable of the plurality of actuation cables.

The medial hip joint 1 may connect a medial left and a medial right part of the medial unilateral exoskeleton 5, 100 so that a left ankle joint 2*a* may be connected to a right side of the medial hip joint and a right ankle joint 2*b* is connected to a left side of the medial hip joint. The medial hip joint 1 may be in the form of a module where the hip joint with pulleys 13*a*, 13*b* is attached to the hip plates 14*a*, 14*b* by one or more supporting rollers. This would advantageously enable a rehabilitation facility to easily exchange a hip joint for a more robust option for a person with a higher body weight.

Figure 5:
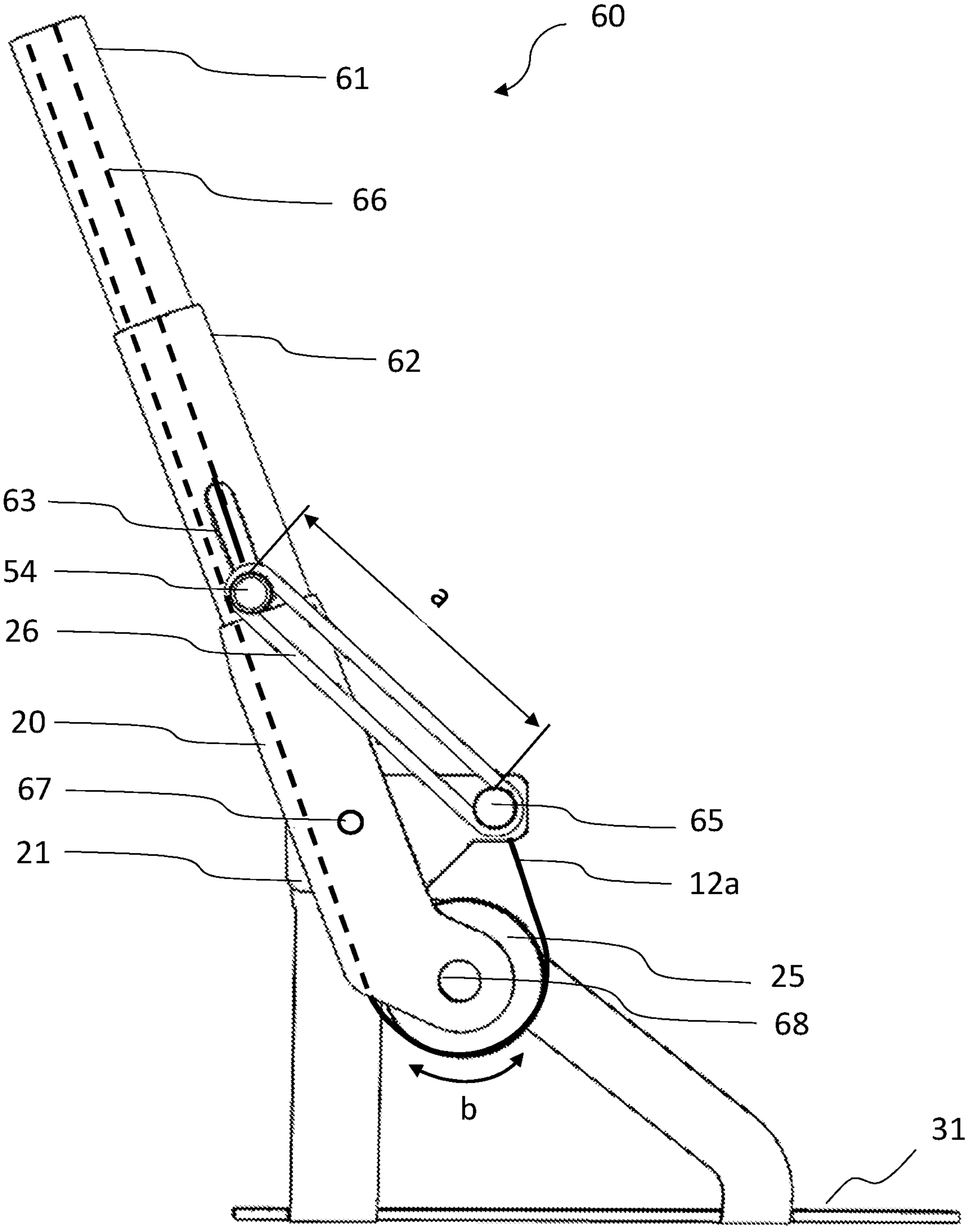
FIG. 5 is a side view depicting another embodiment of an ankle joint usable in the exoskeleton of FIG. 1*a* or 4, with a moveable element in a first end position.
Figure 6:
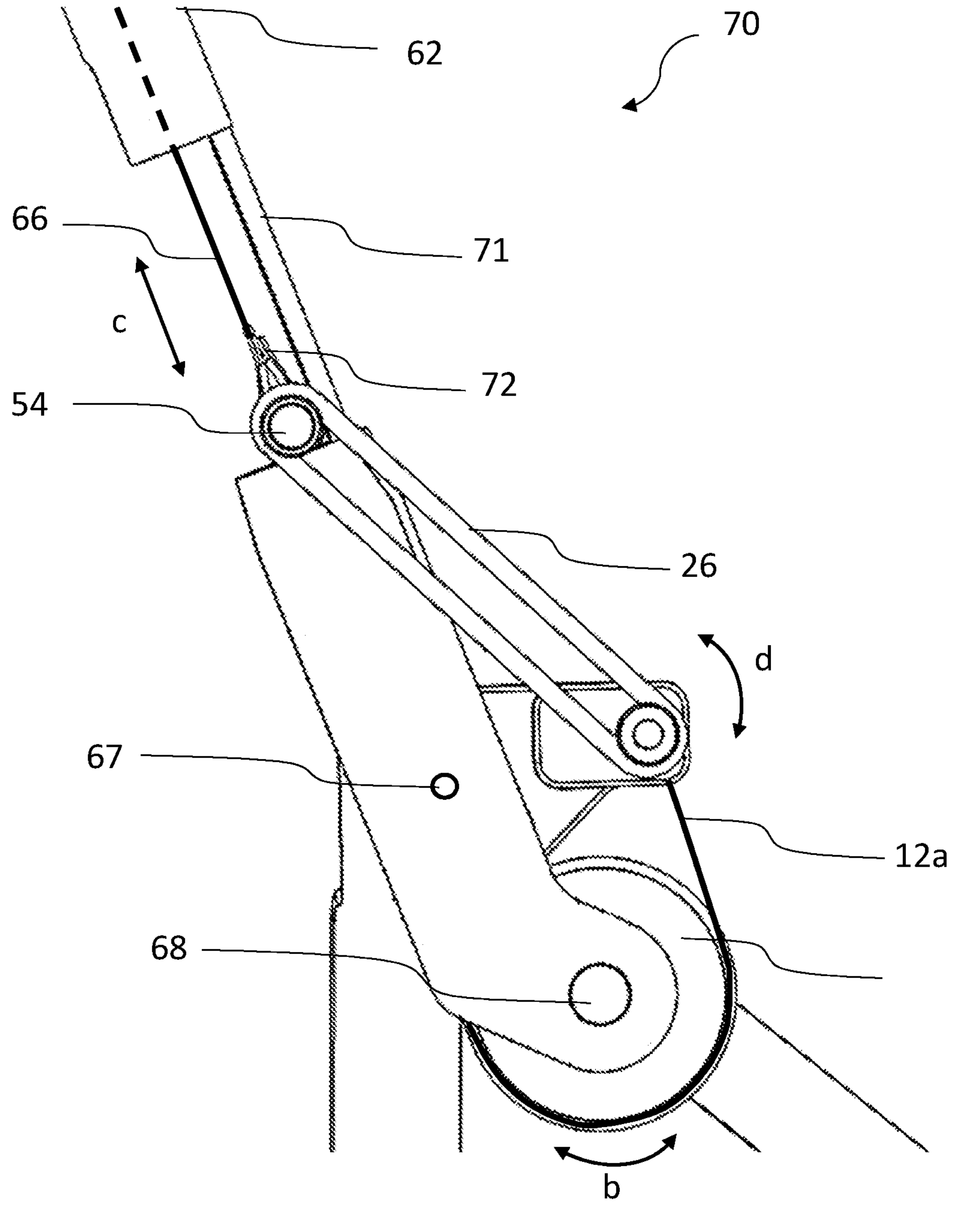
FIG. 6 is a side detail view depicting the embodiment of the ankle joint of FIG. 5, with the moveable element in the first end position.
Figure 7:
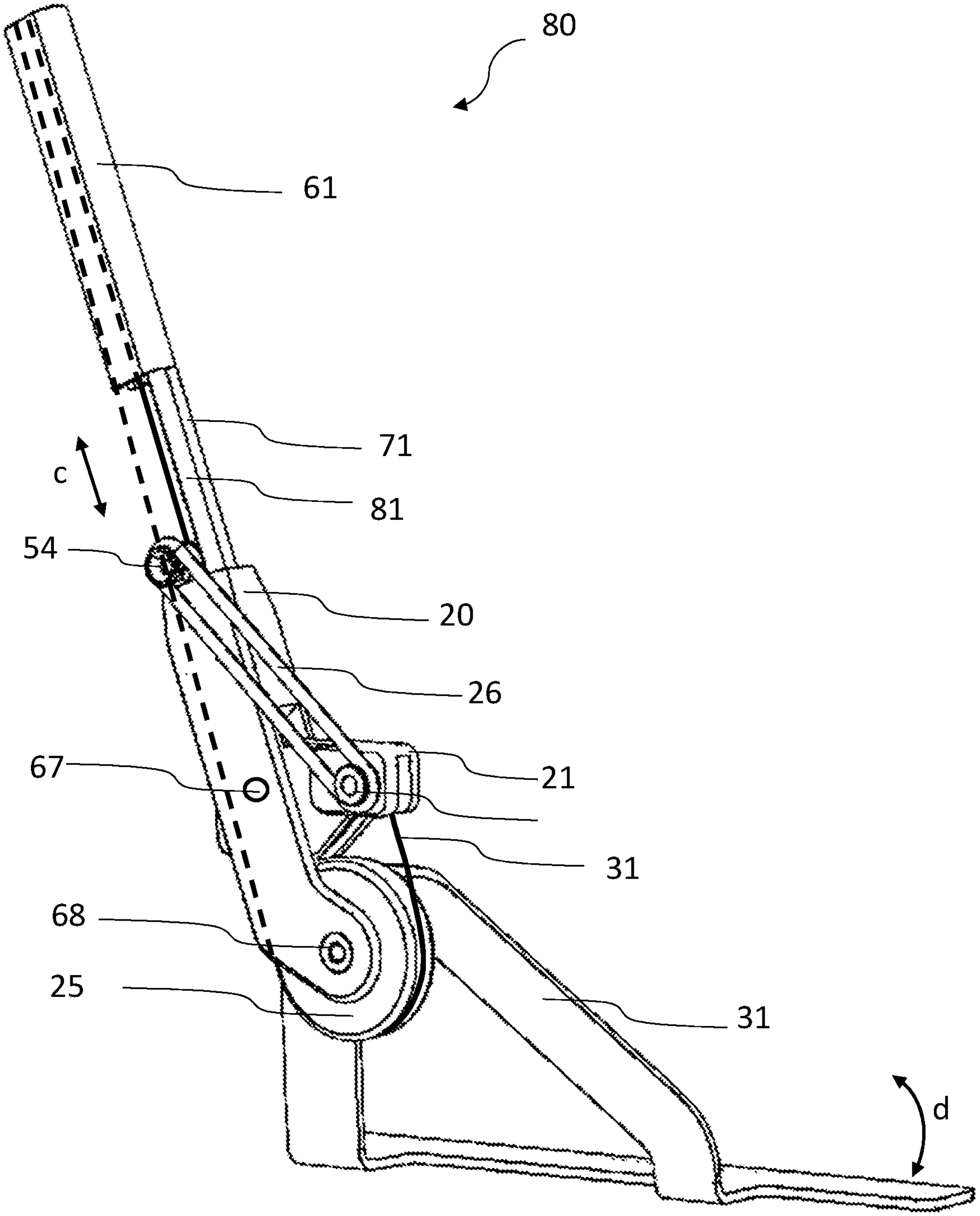
FIG. 7 is a perspective view depicting the embodiment of the ankle joint of FIGS. 5-6, with the moveable element in the first end position.

As explained and further shown in FIG. 3 the replaceable stirrup may be pivotably connected to the ankle joint body 20 via the stirrup coupling 21. The replaceable stirrup may be pivotably connected to the ankle joint body via the ankle pin 22 and the stirrup coupling may pivot about the axis of the ankle pin 22 in direction d. Such pivot may translate into a pivotable movement of the replaceable stirrup 31 in relation to the ankle joint body 20 in direction d. The guide pulley 25, 68 may be coupled to the ankle joint body 20 and configured to support and direct a respective actuation cable 12*a*, 12*b* of the plurality of actuation cables to the stirrup coupling 21. The guide pulley 25, 68 may be connected to the ankle join body 20 via a connection member 68 as shown for instance in FIG. 5. Each of the actuation cables 12*a*, 12*b* may be configured to convey a movement of the hip pulley to the respective ankle joint and cause a pivot of the respective replaceable stirrup in a first direction. Each of the actuation cables 12*a*, 12*b* may be fixed by means of the guide pulley 25, 68 to the stirrup coupling 21. The guide pulley 25, 68 may be configured to guide the respective actuation cable to the stirrup coupling 21. The guide pulley 25, 68 may rotate in direction b and provide a bearing surface to direct a load conveyed by a respective actuation cable to and from the stirrup coupling 21. The actuation cable may be a Bowden cable having a cable holder attached to a respective ankle joint body 20. Each ankle joint 2*a*, 2*b* may be provided with at least one adjustable element 24 formed optionally by an ankle adjusting screw 23 adapted to provide a tension to the respective actuation cable coupled to the ankle joint and impact the angle in the ankle joint.

As depicted in FIG. 2*a* the medial hip joint 1 may be connected to the hip plates 14*a*, 14*b* via a shaft 5. Pulleys may be formed by a left pulley 13*a* and a right pulley 13*b* and each pulley of the left pulley 13*a* and right pulley 13*b* may be connected to one of the two depicted hip plates 14*a*, 14*b* so that a left pulley 13*b* may be connected to a right hip plate 14*b* and the right pulley 13*a* may be connected to a left hip plate 14*a*. Each of the hip plates 14*a*, 14*b* may be connected to one of the two orthosis 3*a*, 3*b* that may be an unilateral type orthosis. The right hip plate 14*b* may be connected to a right unilateral orthosis 3*b* and the left hip plate may be connected to a left unilateral orthosis 3*a*. The left and right pulleys 13*a*, 13*b* may rotate on or with the shaft 5. When the medial unilateral exoskeleton 5, 100, 110 is attached to a person 111 as depicted on FIG. 10 the right pulley 13*a* may be rotate as the left hip 113*a* of the person 111 rotates and the left pulley 13*b* may be rotate along with rotation of the right hip 113*b* of the person 111. Thus, the right pulley 13*a* may be associated with each rotation of the left hip 113*a* and the left pulley 13*b* may be associated with each rotation of the right hip 113*b* as the person 111 moves the hips. As further depicted in FIG. 2*a* the medial hip joint 1 may be provided with at least one adjustable element formed by a hip adjusting screw 18*a*, 18*b*. The at least one adjustable element may be adapted to secure a tension of the actuation cable and impact angle of the respective ankle joint.

The medial hip joint 1 may connect the medial left and right parts of the medial unilateral exoskeleton so that the left ankle joint 2*a* may be connected to a right side of the hip joint and the right ankle joint 2*b* may be connected to the left side of the hip joint. The medial hip joint 1 may be delivered in the form of a module where the hip joint with pulleys may be attached to the hip plates by supporting rollers. One benefit would be to enable rehabilitation facilities to carry out a replacement of one hip joint for a more robust one in the case of person with a higher weight.

The left pulley 13*a* may be connected to the left ankle joint 2*a* by means of a first actuation cable 12*a*. When the first actuation cable 12*a* is actuated it may cause a plantar flexion of a respective left replaceable stirrup 31 and consequently a planar flexion of a shoe 41 that is connected to the left replaceable stirrup 31. Respective elastic member 26 that may connect a respective stirrup coupling 21 and the left ankle joint body 20 may be configured to hold the left replaceable stirrup in a constant dorsal flexion so that the first actuation cable 12*a*, when actuated, acts against the pull force imposed by the elastic member to the replaceable stirrup 31.

The right pulley 13*b* may be connected to the right ankle joint 2*b* by means of a second actuation cable 12*b*. When the second actuation cable 12*b* is actuated it may cause a plantar flexion of a respective right replaceable stirrup 31 and consequently a planar flexion of a shoe 41 that is connected to the right replaceable stirrup 31. Respective elastic member 26 that may connect a respective stirrup coupling 21 and the ankle joint body 20 may be configured to hold the right replaceable stirrup in a constant dorsal flexion so that the second actuation cable 12*b*, when actuated, acts against the pull force imposed by the elastic member to the replaceable stirrup 31.

Due to the contralateral interconnection of the right side of the medial hip joint 1 and a the left ankle joint 2*a* and the left side of the medial hip joint and the right ankle joint 2*b*, the ankle torque (in the direction of the dorsal flexion) may drive the contralateral (opposite) limb when attached to the orthosis to swing forward and propone a step forward.

Each ankle joint 2*a*, 2*b* may be interconnected with a replaceable shoe 41, 105 or a shoe insert. One of the following combinations may be used; a replaceable stirrup with a fixed shoe, a replaceable stirrup with a replaceable shoe or a replaceable stirrup with a fixed insert suitable for an insertion into any footwear. The replaceable stirrup 31 may be firmly integrated (for instance glued and/or secured by a fastener) with a central portion of the shoe sole. A shoe may also be temporarily attached to the stirrup, for instance via a conventional fastening means such as a tape or a Velcro. Alternatively, a shoe insert may be firmly attached to the replaceable stirrup and the insert may then be placed into any shoe and fixed to a foot of a person simply by tying up shoelaces or otherwise securing shoe. Replaceable inserts or shoes enable the medial unilateral exoskeleton to be adapted to an individual person, with respect to the foot size and/or to the preferred type of a footwear, possibly even to other specific requirements.

FIGS. 5 to 8 depict an embodiment of an ankle joint 90 where each of the orthoses further comprises a biasing cable 66 and a moveable member 54. A one end of the elastic member 26 is coupled to the ankle joint body 20 via the moveable member and a one end of the biasing cable 66 is coupled to the moveable member 54. A second end of the biasing cable is coupled to a respective hip pulley 13*a*, 13*b*. A second of the elastic member is coupled to the stirrup coupling 21. The second end of the elastic member 26 may by coupled to the stirrup coupling via a holding member 65. The holding member 65 may be rotatably coupled to the stirrup coupling 21. The biasing cable 66 is adapted to position the moveable member so that the distance a between both ends of the elastic member remains constant. One benefit of maintaining same distance between the opposing ends of the elastic member 26 is a constant tension between the ends of the elastic member 26. The constant tension then may be utilized to create a constant pull force imposed by the elastic member 26 to the replaceable stirrup 21.

Figure 8:
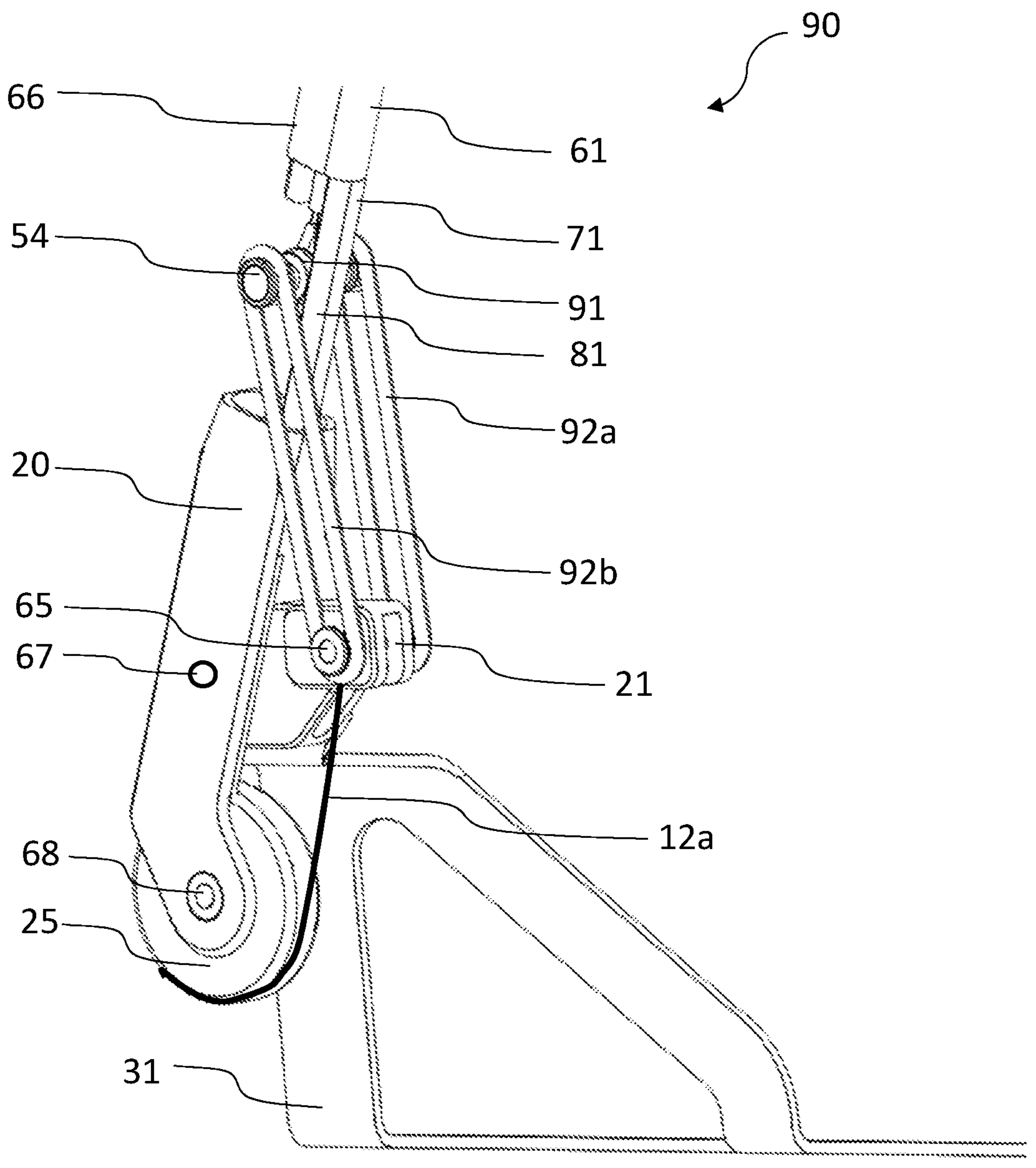
FIG. 8 is a perspective view depicting the embodiment of the ankle joint of FIGS. 5-7, with the moveable element in a second end position.

Each of the orthoses may further comprise a linear guide connected to the moveable member. The linear guide may comprise at least one of a rail linear guide, a linear bearing slide, a ball bearing slide, a rack slide, a dovetail slide or a roller slide. Each of the orthoses may further comprise a hollow first part 62 having a slot 63 and a second part 61. The hollow first part 62 may be coupled to the ankle joint body 20 and a portion of the second part 71 may be inserted within the first part 62. A portion of the moveable member may be guided within the slot 63. The portion of the moveable member may engage the portion 71 of the second part 61 within the hollow first part 62. The hollow first part may be a first hollow profile extending in a longitudinal direction and the second part may be a second hollow profile extending in the longitudinal direction. The second part may be slidably engaged into the first hollow profile. The slot 63 may extend in the longitudinal direction. As shown in FIG. 8 the moveable member 54 may comprise a roller 91 configured to roll on a guiding profile 81 formed in the portion of the second part 71 within the first hollow part and the guiding profile 81 may extend along the longitudinal direction c. The elastic member 26 may be formed by one or more elastic elements shaped as a belt, a band, a string, a ring, a rope or a spring or a combination thereof. The movable member may extend between two ends perpendicular to the longitudinal direction. The medial unilateral exoskeleton may include two elastic members 92*a*, 92*b* which are attached to the ends of the moveable member. One benefit of such arrangement may be to counterbalance roller 91 engaging the guiding profile. Another benefit may be a redundancy of the elastic members as when one of the elastic members is to fail for instance due to is rupture the second elastic member will be able to keep pivotal preload of the stirrup coupling 21 in relations to ankle body.

Figure 9:
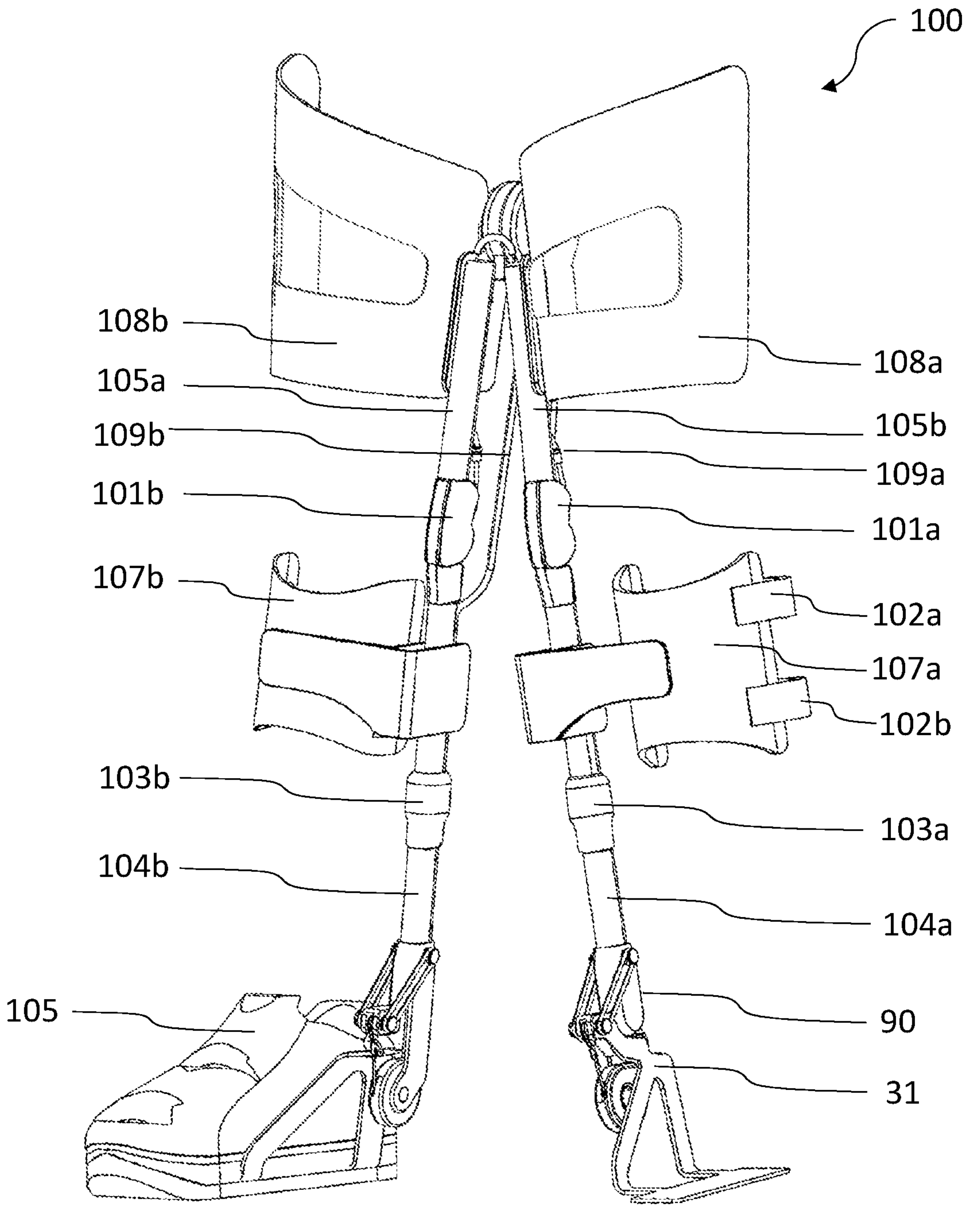
FIG. 9 is a perspective view depicting another embodiment of a medial unilateral exoskeleton.

FIGS. 9 and 10 depict an exemplary embodiment of a medial unilateral exoskeleton comprising a thigh cuffs 108*a*, 108*b* each adapted for an attachment to a thigh 112*a*, 112*b* of a person 111. Actuation cables 109*a*, 109*b* may be partially embedded into hollow parts of orthoses. Such hollow parts may be medial lower leg upright 104*a*, 104*b* and/or medial thigh upright 105*a*, 105*b*. The medial lower leg upright 104*a*, 104*b* and medial thigh upright 105*a*, 105*b* may at least partially to fit to each other. Length adjusting member shown 103*a*, 103*b* may be configured to control the partial fit of the medial lower leg upright 104*a*, 104*b* and medial thigh upright 105*a*, 105*b* and so the length adjusting member is able to control length of the medial thigh upright 105*a*, 105*b* and/or the medial lower leg upright 104*a*, 104*b*. The medial unilateral exoskeleton may further comprise knee joints 101*a*, 101*b* that may be adapted to lock the medial thigh upright 105*a*, 105*b* and the lower leg upright 104*a*, 104*b* rigidly together. The medial unilateral exoskeleton may further comprise lower leg cuffs 107*a* and 107*b*, the lower leg cuffs being adapted to the body proportions of a particular person. Each of the lower leg cuffs may have one or more attachment members 102*a*, 102*b* adapted to attached respective lower leg cuff to a leg of a person.

When using the medial unilateral exoskeleton and its variety as described above the orthoses 3*a*, 114*a*, 3*b*, 114*b* are connected respectively to a right and a left lower limb of a person and the shoe 41, 105 or a shoe insert 41 is connected to a foot of the person.

Such medial unilateral exoskeleton of the present disclosure may be used with crutches, walkers, or parallel walkways. The medial unilateral exoskeleton of the present disclosure is affordable, easy to assemble and maintain, and easy to use. The medial unilateral exoskeleton of the present invention also provides an increased stability and enables safer training of users. The medial unilateral exoskeleton of the present disclosure may be used in a home care because of its easy deployment and relatively simple control which does not require a special assistance from a third party.

Example 1

In an example a medial unilateral exoskeleton as outlined in previous embodiments may be used as a user specific medial unilateral exoskeleton. Such user specific exoskeleton may comprise a medial hip joint 1 comprising hip plates 14*a*, 14*b*, a shaft 15 and pulleys 13*a*, 13*b* connected through a unilateral medial thigh upright 4 via the hip plates 14*a*, 14*b* to a right and a left lower orthosis. Each of the lower limb orthoses 3*a*, 3*b* may comprise, in addition to a metal hollow medial thigh upright 4 having an oval cross section, a thigh cuff 5 comprising two thigh bands 9 connected by a lateral support element 1. Each of the thigh cuffs 5 may be made of a steel thin flat plate provided with a padding and with a Velcro type fastening for an attachment of the thigh cuff to a user's leg. The skeleton may further comprise two self-locking knee joints 6 and two hollow unilateral medial lower leg upright 7 with an oval cross section. Each of the hollow unilateral medial lower leg uprights 7 may be provided with one lower leg cuff 8 in the form of an arc made of a steel thin flat plate provided with a padding and with a Velcro type fastening for an attachment to the user's leg. The length of the each of unilateral medial thigh uprights 4 and the unilateral medial lower leg uprights 7, the circumference of the thigh cuffs 5 and the lower leg cuffs 8 may be adapted to the body proportions of a particular person. Each of the lower limb orthoses 3*a*, 3*b* further comprises an ankle joint 2*a* 2*b* connected to the pulleys 13*a*, 13*b* of the hip joint 1 by means of actuation cables 12*a*, 12*b*. The actuation cables may be attached on one end to the respective pulley 13*a*, 13*b* of the hip joint 1 and on second end to the stirrup coupling 21 of the respective ankle joints 2*a*, 2*b*. The ankle joint body 20 may be further coupled to the stirrup coupling 21 by an elastic element 26. The stirrup coupling 21 of the respective ankle joint 2*a*, 2*b* may rotate on a pin 22 of the ankle joint body 2*a*, 2*b*. Each of the orthosis 3*a*, 3*b* may further comprise a replaceable stirrup 31 that may be connected to an orthopedic shoe 41 of a size corresponding to the leg size of the particular person. Each of the actuation cables 12*a*, 12*b* is a Bowden cable that may be attached to a Bowden holder 16 and may be guided partially inside the hollow medial thigh upright 4 and the hollow unilateral medial lower leg upright 7.

Such medial unilateral exoskeleton may be applied by a hip joint 1 between the legs of a seated user. The thigh cuffs 5 may be then attached to the particular user thighs via the thigh bands 9 and the lower leg uprights 7 may be attached to user's calf's via use of one or more lower leg cuffs 8. When the user reaches the vertical position, the thigh plate 4 and the lower leg uprights 7 may be locked at the knee joint 6 so as to hold the user in a vertical position without the possibility of a rotation in the knee joint. Due to the contralateral connection of the left ankle joint with a right hip joint and the right ankle joint with a left hip joint, one foot and associated dorsal flexion contralaterally swings the other limb, reducing effort and allowing the user to move reduced energy intensity and train walking and verticalization. After training in the rehabilitation facility, the user is able to use the medial unilateral exoskeleton using crutches or walkers without the assistance of medical staff.

Example 2

In another example a medial unilateral exoskeleton as outlined in previous embodiments may be used in a healthcare and/or rehabilitation facility. Such universal medial unilateral exoskeleton may comprise a medial hip joint 1 comprising hip plates 14*a*, 14*b*, a shaft 15 and pulleys 13*a*, 13*b* that may be covered by pulley support covers 17*a*, 17*b*. The medial hip joint may be connected via hip plates 14*a*, 14*b* to orthoses 3*a*, 3*b* of a right and a left lower limb of a person, specifically through the unilateral medial thigh upright 4. Each of the lower limb orthoses 3*a*, 3*b* my include, a medial thigh upright 4 with an oval cross-section, a thigh cuff 5 that may comprise two thigh bands 9 interconnected by a lateral support element 10, the thigh cuff 5 that may be made of thin steel plate. The thigh cuff 5 may be provided with a padding and with a fastening for an attachment of the thigh cuff to a person leg. Each of the orthoses may be further provided with a self-locking knee joint 6, a unilateral medial lower leg upright 7 that may have an oval cross section provided with a one lower leg cuff 8 that may be in the form of a steel thin flat plate provided with a padding and with a Velcro type fastening for an attachment to the person's leg. The length of the medial lower leg upright 7 may be adjustable. The circumference of the thigh cuffs 5 and the lower leg cuff 8 may also be adjustable. Lateral hip joints 51 may be attached to the thigh cuffs 5, to which a lumbar brace 52 may be attached. Each of the lower limb orthoses 3*a*, 3*b* may further include an ankle joint 2*a*, 2*b* connected to the pulleys 13*a*, 13*b* of the hip joint 1 by means of actuation cables 12*a* 12*b*. The actuation cables may be attached on one end to the respective pulley 13*a*, 13*b* of the hip joint 1 and on second end to the stirrup coupling 21 of the respective ankle joints 2*a*, 2*b*.

The ankle joint body 20 may be further coupled to the stirrup coupling 21 by an elastic element 26. The stirrup coupling 21 of the respective ankle joints 2*a*, 2*b* rotates on a pin 22 of the ankle joint body 2*a*, 2*b*. Each of the orthoses 3*a*, 3*b* may further comprise a replaceable stirrup 31 connected to an orthopedic shoe 41. Each of the actuation cables 12*a*, 12*b* may be a Bowden cable that may be attached to a Bowden holder 16 and guided partially inside the hollow medial thigh upright 4 and the hollow unilateral medial lower leg uprights 7. The actuation cables 12*a*, 12*b* may be replaceable depending on the length required, which is influenced by the adjustment of the length of the medial lower leg upright 7. In the area of the ankle joints 2*a*, 2*b* may be located adjustment screws 23 of the actuation cable 12*a*, 12*b* that affect the angle in the ankle joint 2*a*, 2*b*. A sliding adjustable bar 27 may be formed on the stirrup coupling 21 to influence the transmission ratio between the hip and ankle, further influencing the walking style. In the region of the medial hip joint 2*a*, 2*b*, an adjustable element may be provided in the form of a hip adjusting screw 18*a*, 18*b* of the actuation cable 12*a*, 12*b*. The adjustable element may provide a tension to the actuation cable and affects the angle in the ankle joint 2*a*, 2*b*.

The universal medial unilateral exoskeleton may be applied by a hip joint 1 between the legs of a seated user, with the thigh cuffs 5 attached to the persons thighs via the thigh bands 9. The lower leg uprights 7 may be attached to the person calves via one or more lower leg cuffs 8. Next, the lateral hip joint 51 may be attached to the sides of the seated person and the lumbar brace 52 may be attached to the person's body. After the person reaches a vertical position, the medial thigh upright 4 and the lower leg upright 7 may be locked at the knee joint 6 so as to hold the user in a vertical position without the possibility of a rotation within the knee joint. Due to the contralateral connection of the left ankle joint with the right hip joint and the right ankle joint with the left hip joint, one foot and associated dorsal flexion contralaterally swings the other limb, reducing effort and allowing the user to move reduced energy intensity and train walking and verticalization.

While various spatial and directional terms, such as top, bottom, lower, mid, lateral, horizontal, vertical, front and the like may be used to describe embodiments of the present disclosure, it is understood that such terms are merely used with respect to the orientations shown in the drawings. The orientations may be inverted, rotated, or otherwise changed, such that an upper portion is a lower portion, and vice versa, horizontal becomes vertical, and the like.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments of the disclosure without departing from their scope. While the dimensions and types of materials described herein are intended to define the parameters of the various embodiments of the disclosure, the embodiments are by no means limiting and are exemplary embodiments. Many other embodiments will be apparent to those of skill in the art upon reviewing the above description. The scope of the various embodiments of the disclosure should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f), unless and until such claim limitations expressly use the phrase "means for" followed by a statement of function void of further structure.

This written description uses examples to disclose the various embodiments of the disclosure, including the best mode, and also to enable any person skilled in the art to practice the various embodiments of the disclosure, including making and using any devices or systems and performing any incorporated methods. The patentable scope of the various embodiments of the disclosure is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal languages of the claims.

What is claimed:

1. A medial unilateral exoskeleton configured to abut lower limbs from the Inner side, the exoskeleton comprising:

a single medial hip joint comprising hip plates and hip pulleys, wherein the single medial hip joint is configured to be positioned between the lower limbs;

a plurality of actuation cables;

orthoses suitable for a right and a left lower limb of a person, the orthoses comprise a left orthosis and a right orthosis each being coupled to one side of the single medial hip joint and each of the orthoses comprising an ankle joint having a replaceable stirrup with a shoe or a shoe insert, a stirrup coupling, an ankle joint body and a guide pulley, wherein each of the hip pulleys is coupled to a respective ankle joint by at least one actuation cable of the plurality of actuation cables so that each actuation cable is on one end attached to one of the hip pulleys and on a second end attached to the stirrup coupling of the respective ankle joint, wherein the replaceable stirrup is pivotably connected to the ankle joint body via the stirrup coupling, wherein the guide pulley is coupled to the ankle joint body and configured to support and direct a respective actuation cable of the plurality of actuation cables to the stirrup coupling, wherein each of the actuation cables is configured to convey a movement of the hip pulley to the respective ankle joint and cause a pivot of the respective replaceable stirrup in a first direction.

2. The medial unilateral exoskeleton of claim 1, wherein each of the orthoses further comprises at least one elastic member having a one end coupled to the ankle joint body and a second end coupled to the stirrup coupling, wherein the at least one elastic member is adapted to act in a second direction opposite to the first direction caused by the movement conveyed by the respective actuation cable.

3. The medial unilateral exoskeleton of claim 2, wherein each of the orthoses further comprises a biasing cable and a moveable member, wherein the one end of the elastic member is coupled to the ankle joint body via the moveable member, wherein a one end of the biasing cable is coupled to the moveable member and a second end of the biasing cable is coupled to the hip pulley, wherein the biasing cable is adapted to position the moveable member so that the distance between both ends of the elastic member remains constant.

4. The medial unilateral exoskeleton of claim 3, wherein each of the orthoses further comprises a linear guide connected to the moveable member.

5. The medial unilateral exoskeleton of claim 4, wherein the linear guide comprises at least one of a rail linear guide, a linear bearing slide, a ball bearing slide, a rack slide, a dove-tail slide or a roller slide.

6. The medial unilateral exoskeleton of claim 3, wherein each of the orthoses further comprises a hollow first part having a slot and a second part, wherein the hollow first part is coupled to the ankle joint body, wherein a portion of the second part is inserted within the first part, wherein a portion of the moveable member is guided within the slot and configured to engage the portion of the second part within the hollow first part.

7. The medial unilateral exoskeleton of claim 6, wherein the first part is a first hollow profile extending in a longitudinal direction, the second part is a second hollow profile ex-tending in the longitudinal direction and is slidably engaged into the first hollow profile, the slot extends in the longitudinal direction.

8. The medial unilateral exoskeleton of claim 7, wherein the moveable member comprises a roller configured to roll on a guiding profile formed in the portion of the second part within the first hollow part, the guiding profile extending along the longitudinal direction.

9. The medial unilateral exoskeleton of claim 7, wherein the movable member extends between two ends perpendicular to the longitudinal direction, and the medial unilateral exoskeleton includes two elastic members which are attached to the ends of the mov able member.

10. The medial unilateral exoskeleton of claim 2, wherein the elastic member is formed by one or more elastic elements shaped as a belt, a band, a string, a rope or a spring or a combination thereof.

11. The medial unilateral exoskeleton of claim 1, wherein each actuation cable is either a pull cable or a push-pull cable and each actuation cable has a solid or a wire rope core.

12. The medial unilateral exoskeleton of claim 1, wherein each of the actuation cables or at least one actuation cable of the plurality of actuation cables is a Bowden cable.

13. The medial unilateral exoskeleton of claim 1, wherein each of the hip pulleys is coupled to a respective ankle joint by means of one actuation cable of the plurality of actuation cables.

14. The medial unilateral exoskeleton of claim 1, wherein each of the orthoses further comprises a unilateral medial thigh upright, a thigh cuff comprising one or more thigh bands, a knee joint, a unilateral medial lower leg upright and at least one lower leg cuff.

15. The medial unilateral exoskeleton of claim 14, wherein the knee joint is a self-locking joint.

16. The medial unilateral exoskeleton of claim 14, wherein each of the actuation cables is at least partially embedded within the medial lower leg upright and/or the medial thigh upright.

17. The medial unilateral exoskeleton of claim 14, wherein the medial thigh upright and/or the medial lower leg upright have an adjustable length.

18. The medial unilateral exoskeleton of claim 1, wherein the ankle joint is provided with at least one adjustable element formed by an ankle adjusting screw adapted to provide a tension to the actuation cable coupled to the ankle joint and impact the angle in the ankle joint.

19. The medial unilateral exoskeleton of claim 1, wherein the medial hip joint is provided with at least one adjustable element formed by a hip adjusting screw, wherein the at least one adjustable element is adapted to secure a tension of the actuation cable and impact an angle of the ankle joint.

20. The medial unilateral exoskeleton of claim 1, further comprising a lumbar ortho-sis coupled to the medial hip joint or a lateral hip joint.

* * * * *